(12) United States Patent
Yamaguchi et al.

(10) Patent No.: US 9,839,708 B2
(45) Date of Patent: Dec. 12, 2017

(54) METHOD FOR TREATING USED ABSORBENT ARTICLE

(71) Applicant: Unicharm Corporation, Ehime (JP)

(72) Inventors: Masashi Yamaguchi, Kagawa (JP); Takayoshi Konishi, Kagawa (JP); Toru Oba, Kagawa (JP)

(73) Assignee: Unicharm Corporation, Ehime (JP)

( * ) Notice: Subject to any disclaimer, the term of this patent is extended or adjusted under 35 U.S.C. 154(b) by 106 days.

(21) Appl. No.: 14/435,130

(22) PCT Filed: Oct. 9, 2013

(86) PCT No.: PCT/JP2013/077533
§ 371 (c)(1),
(2) Date: Apr. 10, 2015

(87) PCT Pub. No.: WO2014/057994
PCT Pub. Date: Apr. 17, 2014

(65) Prior Publication Data
US 2015/0265737 A1    Sep. 24, 2015

(30) Foreign Application Priority Data
Oct. 12, 2012   (JP) ................ 2012-227517

(51) Int. Cl.
*A61L 2/18* (2006.01)
*A61L 11/00* (2006.01)
(Continued)

(52) U.S. Cl.
CPC ............. *A61L 2/18* (2013.01); *A61L 11/00* (2013.01); *B09B 3/00* (2013.01); *B09B 3/0075* (2013.01);
(Continued)

(58) Field of Classification Search
CPC ...................................... A61L 12/18
(Continued)

(56) References Cited

U.S. PATENT DOCUMENTS 6,319,390 B1 * 11/2001 Kono et al. .......... 205/701
7,387,719 B2    6/2008 Carson et al.
(Continued)

FOREIGN PATENT DOCUMENTS

JP  2004-313878 A   11/2004
JP  2005-334321 A   12/2005
(Continued)

OTHER PUBLICATIONS

English translation of Document No. JP 2007303047 provided by Japan Platform for Patent Information (www.j-platpat.inpit.go.jp), Nov. 22, 2007.*
(Continued)

*Primary Examiner* — Kevin Joyner
*Assistant Examiner* — Holly Mull
(74) *Attorney, Agent, or Firm* — Brinks Gilson & Lione (57) ABSTRACT

Provided is a method for treating a used absorbent article, this method being hygienic and capable of recovering recyclable material with a high degree of safety. This method for treating a used absorbent article is characterized by including (a) an acidic electrolyzed water treatment step that treats the used absorbent article in a treatment tank that has acidic electrolyzed water serve as a treatment fluid. This method preferably further includes (b) an alkaline electrolyzed water treatment step that treats the used absorbent article in a treatment tank that has alkaline electrolyzed water as a treatment fluid.

4 Claims, 2 Drawing Sheets

(51) Int. Cl.
 B09B 3/00 (2006.01)
 B29B 17/02 (2006.01)
 B29L 31/48 (2006.01)
 A61F 13/84 (2006.01)
(52) U.S. Cl.
 CPC .............. B29B 17/02 (2013.01); *A61F 13/84* (2013.01); *B29B 2017/0293* (2013.01); *B29B 2017/0296* (2013.01); *B29L 2031/4878* (2013.01); *Y02W 30/622* (2015.05)
(58) Field of Classification Search
 USPC ......................................................... 422/37
 See application file for complete search history.

(56) References Cited

U.S. PATENT DOCUMENTS

2003/0024828 A1\* 2/2003 Kondo .................... A61L 2/035
 205/742
2011/0030907 A1\* 2/2011 Nakamoto ............. D21C 5/027
 162/5

FOREIGN PATENT DOCUMENTS

| JP | 2005-336337 A | 12/2005 |
| JP | 2005-342570 A | 12/2005 |
| JP | 2007303047 A \* | 11/2007 |
| JP | 2009-183893 A | 8/2009 |
| JP | 2010-84031 A | 4/2010 |

OTHER PUBLICATIONS

Osada et al., Gels handbook, 2001, Academic Press, vol. 1, p. 26-27.\*
English Translation of Document No. JP 2005342570 A provided by proquest.com: Sanitary article dissolving treating apparatus; Dec. 15, 2005.\*
Klungness et al., Feasibility of recycling post-consumer diapers, May 1992, Progress in Paper Recycling, pp. 49-59.\*
International Search Report from corresponding PCT application No. PCT/JP2013/077533 dated Jan. 7, 2014 (2 pg).

\* cited by examiner

METHOD FOR TREATING USED ABSORBENT ARTICLE

RELATED APPLICATION

This application is a 35 U.S.C. §371 national phase filing of International Patent Application No. PCT/JP2013/077533, filed Oct. 9, 2013, through which and to which priority is claimed under 35 U.S.C. §119 to Japanese Patent Application No. 2012-227517, filed Oct. 12, 2012, the complete disclosure of which is hereby expressly incorporated by reference.

TECHNICAL FIELD

The present invention relates to a method for treating used absorbent articles.

BACKGROUND ART

Research and development are being actively conducted on recycling technology for converting finished products into raw materials and reusing them as materials of new products. Absorbent articles such as disposable diapers, incontinence pads, incontinence liners, sanitary napkins or panty liners are sanitary articles, and although they have typically been disposed of by incineration and the like following use, in response to changes in environmental awareness in recent years, there has been a growing demand to recycle such sanitary articles.

For example, Patent Document 1 proposes a disposable diaper treatment method for treating used disposable diapers by disinfecting, comprising: placing used disposable diapers in a treatment tank along with lime and hypochlorous acid, agitating over a prescribed amount of time while supplying the minimum amount of water that enables agitation in the treatment tank, discharging and dehydrating liquid in the treatment tank to outside the treatment tank, recovering the discharged wastewater, and discarding the discharged wastewater after subjecting to water treatment.

PRIOR ART DOCUMENTS

Patent Documents

Patent Document 1: Japanese Unexamined Patent Publication No. 2010-84031

DISCLOSURE OF THE INVENTION

Problems to be Solved by the Invention

In Patent Document 1, however, since an amount of lime is added that is sufficient for decomposing the high molecular weight polymer in the disposable diaper, the pH in the treatment tank becomes high, and as a result, unless the treatment tank is repeatedly rinsed using a large amount of water, safety cannot be assured, thereby potentially preventing the recovered material (pulp) from being reused as a sanitary material. In addition, although an ozone or a chlorine-based compound is used as disinfectant (bactericide) in Patent Document 1, since the bactericidal activity of ozone is of short duration despite having a high degree of bactericidal activity capable of disinfecting in a short period of time, ozone must be continued to be regenerated throughout treatment, and although it is used to disinfect at low concentrations, since a high concentration is required in order to obtain washing and bleaching effects, problems remain with respect to safety and the like in terms of handling. Although chlorine-based compounds allow the obtaining of bactericidal effects at low concentrations, since they are required to be used at high concentrations in the case of attempting to wash and bleach articles soiled with protein-based substances, their use at high concentrations is not desirable in absorbent article applications from the viewpoint of remaining in the recycled material.

Therefore, an object of the present invention is to provide a method for treating used absorbent articles that enables the recovery of hygienic and highly safe recycled materials.

Means for Solving the Problems

In order to solve the aforementioned problems, the present invention provides a method for treating used absorbent articles comprising: (a) an acidic electrolyzed water treatment step for treating a used absorbent article in a treatment tank that uses acidic electrolyzed water for the treatment liquid.

Effects of the Invention

According to the present invention, a method is provided for treating used absorbent articles that is hygienic and enables the recovery of highly safe recycled materials.

BEST MODE FOR CARRYING OUT THE INVENTION

The following provides an explanation of the method for treating used absorbent articles according to the present invention. The method of the present invention relates to a method for treating used absorbent articles, the method comprising: (a) an acidic electrolyzed water treatment step for treating the used absorbent article in a treatment tank that uses acidic electrolyzed water for the treatment liquid.

The method for treating used absorbent articles according to the present invention is a method that demonstrates superior washing function and exhibits bactericidal effects. The method for treating used absorbent articles according to the present invention also enables the recovery of hygienic and highly safe recycled materials such as recycled pulp. The residual chlorine content of recycled materials such as recycled pulp is either not detected or less than 1 ppm and the pH thereof is within the range of 3.1 to 9.8.

There are no particular limitations on the treatment tank used in the method for treating used absorbent articles according to the present invention provided it can contain water or a treatment liquid such as acidic electrolyzed water or alkaline electrolyzed water and the like. The treatment tank used in the method for treating used absorbent articles according to the present invention may be a container, and examples thereof include a cylindrical container, a pipe-shaped container or a tub-shaped container.

The acidic electrolyzed water and alkaline electrolyzed water to be subsequently described that are used in the method for treating used absorbent articles according to the present invention can be generated by electrolyzing saltwater. Acidic electrolyzed water is generated on the anode side while alkaline electrolyzed water is generated on the cathode side.

The formation reaction formulas of the acidic electrolyzed water (anode reaction) and alkaline electrolyzed water (cathode reaction) are as indicated below.

Anode Reaction:

$$2Cl^- \rightarrow Cl_2 + 2e^- \quad (1)$$

$$2H_2O \rightarrow O_2 + 4H^+ + 4e^- \quad (2)$$

Cathode Reaction:

$$2H_2O + 2e^- \rightarrow H_2 + 2OH^- \quad (3)$$

Chlorine Gas Reaction:

$$Cl_2 + H_2O \rightarrow HClO + H^+ + Cl^- \quad (4)$$

According to the aforementioned formulas (1), (2) and (4), chlorine gas is dissolved in acidic electrolyzed water and microorganisms and the like can be disinfected by the action of the hypochlorous acid formed from this chlorine gas. The chlorine concentration in the acidic electrolyzed water is preferably 20 ppm to 70 ppm. Chlorine concentration can be measured using, for example, the Model CL-5F Chlorine Ion Meter (Kasahara Chemical Instruments Co., Ltd.). On the other hand, alkaline electrolyzed water contains sodium hydroxide (NaOH) according to the aforementioned formula (3), can be used to remove protein-based and oily soiling, and is able to disperse and eliminate protein-based and oily soiling by osmotic action.

The pH of the acidic electrolyzed water is preferably 2.5 to 5.0, while the pH of the alkaline electrolyzed water is preferably 11 to 12.5. The pH of the acidic electrolyzed water and alkaline electrolyzed water can be measured using, for example, the Model AS-212 pH Meter manufactured by As One Corp.

Examples of used absorbent articles in the method for treating used absorbent articles of the present invention include hygienic articles and sanitary articles such as disposable diapers, incontinence pads, incontinence liners, sanitary napkins and panty liners, and these may be targeted for use by humans or may be targeted for use by animals other than humans such as pets. Although there are no particular limitations on the absorption targets of the used absorbent articles, they primarily consist of menstrual blood, urine, stool and the like.

In many cases, the used absorbent article in the method for treating used absorbent articles of the present invention is composed of an absorbent body, plastic or nonwoven fabric and the like, wherein the absorbent body is obtained by mixing pulp and a superabsorbent polymer (to be abbreviated as "SAP").

An example of a superabsorbent polymer is a swellable crosslinked polymer obtained by polymerizing a hydrophilic monomer. Although there are no particular limitations on the structure or composition thereof, specific examples include partially neutralized, crosslinked polyacrylic acid polymers, crosslinked, partially neutralized starch-acrylic acid graft polymers, isobutylene-maleic acid copolymers, saponified vinyl acetate-acrylic acid copolymers, hydrolysis products of acrylamide and a (co)polymer, hydrolysis products of acrylonitrile polymers, and (meth)acrylamide derivatives. Among these, polyacrylate-based crosslinked polymers are preferable. 50 mol % to 90 mol % of the acid radicals in the polyacrylate-based crosslinked polymer are preferably neutralized, and examples of the resulting salts are alkaline metal salts, ammonium salts and amine salts.

The method for treating used absorbent articles of the present invention preferably further comprises (b) an alkaline electrolyzed water treatment step for treating the used absorbent article in a treatment tank containing alkaline electrolyzed water for the treatment liquid (Aspect 1). According to Aspect 1, washing function is further improved, bactericidal action is further improved, the residual level of chlorine in the recycled material such as recycled pulp is not detected (less than 1 ppm), and pH is within the range of 3.1 to 9.8.

In Aspect 1, the alkaline electrolyzed water treatment step (b) is preferably a step carried out prior to the acidic electrolyzed water treatment step (a) (Aspect 2). According to Aspect 2, washing function is further improved, bactericidal action is further improved, the residual level of chlorine in the recycled material such as recycled pulp is not detected (less than 1 ppm), and pH is within the range of 3.1 to 9.8. According to Aspect 2, since protein-based or oily soiling is removed and eliminated from the used absorbent article in the alkaline electrolyzed water treatment step (b), and the protein-based or oily soiling can be discharged outside the treatment step after going through the subsequent acidic electrolyzed water treatment step (a) and/or rinsing step to be subsequently described, removal efficiency of protein-based or oily soiling can be enhanced.

In Aspect 1, the alkaline electrolyzed water step (b) is preferably carried out after the acidic electrolyzed water treatment step (a) (Aspect 3). According to Aspect 3, washing function is further improved, the residual level of chlorine in the recycled material such as recycled pulp is not detected (less than 1 ppm), and pH is within the range of 3.1 to 9.8.

The method for treating used absorbent articles of the present invention preferably further comprises a step (c1) for introducing metal ions into the treatment tank that uses acidic electrolyzed water for the treatment liquid (Aspect 4). According to Aspect 4, in addition to the aforementioned effects, moisture contained in a superabsorbent polymer that composes the used absorbent article can be further dehydrated and removed. Since dehydration and removal of moisture contained in the superabsorbent polymer facilitates sedimentation of the superabsorbent polymer, the treatment efficiency (such as washing efficiency, disinfecting efficiency or rinsing efficiency) of the acidic electrolyzed water treatment step, alkaline electrolyzed water treatment step and rinsing step and the like can be further enhanced.

Although there are no particular limitations on the metal ions provided they are metal ions, examples thereof include alkaline metal ions, alkaline metal salts, alkaline earth metal ions, alkaline earth metal salts, transition metal ions and transition metal salts.

Examples of alkaline metal ions include lithium ions, sodium ions, potassium ions, rubidium ions and cesium ions. Examples of alkaline metal salts include water-soluble salts of lithium, sodium, potassium rubidium and cesium, and more particularly, include sodium chloride, potassium chloride, sodium nitrate, potassium nitrate, sodium sulfate and potassium sulfate.

Examples of alkaline earth metal ions include beryllium ions, magnesium ions, calcium ions, strontium ions and barium ions. Examples of alkaline earth metal salts include water-soluble salts of beryllium, magnesium, calcium, strontium and barium, and more particularly, include calcium oxide (lime), calcium chloride, calcium nitrate, magnesium chloride and magnesium nitrate.

Examples of transition metal ions include iron ions, cobalt ions, nickel ions and copper ions. Examples of transition metal salts include water-soluble salts of iron, cobalt, nickel and copper, and salts of inorganic acids, salts of organic acids or complexes and the like may also be used provided they can be incorporated in a water absorbent polymer. Examples of salts of inorganic acids include iron salts such as iron chloride, iron sulfate, iron phosphate or iron nitrate, cobalt salts such as cobalt chloride, cobalt sulfate, cobalt phosphate or cobalt nitrate, nickel salts such as nickel chloride or nickel sulfate, and copper salts such as copper chloride or copper sulfate. Examples of salts of organic acids include iron lactate, cobalt acetate, cobalt stearate, nickel acetate and copper acetate.

The amount of alkaline metal ion or alkaline metal salt is preferably 8 millimoles or more, more preferably 9 millimoles to 20 millimoles and even more preferably 10 millimoles to 16 millimoles per gram (dry weight) of superabsorbent polymer that composes the used absorbent article. The amount of alkaline earth metal ion, alkaline earth metal salt, transition metal ion or transition metal salt is preferably 4 millimoles or more, more preferably 4.5 millimoles to 10 millimoles and even more preferably 5 millimoles to 8 millimoles per gram (dry weight) of superabsorbent polymer that composes the used absorbent article. If the amount of alkaline metal ion, alkaline metal salt, alkaline earth metal ion, alkaline earth metal salt, transition metal ion or transition metal salt is excessively low, dehydration of the superabsorbent polymer becomes inadequate. If the amount of alkaline metal ion, alkaline metal salt, alkaline earth metal ion, alkaline earth metal salt, transition metal ion or transition metal salt is excessively high, since excess alkaline metal ion, alkaline earth metal ion or transition metal ion remains in the treatment liquid without being incorporated into the superabsorbent polymer, this leads to wasteful use of alkaline metal ion, alkaline metal salt, alkaline earth metal ion, alkaline earth metal salt, transition metal ion or transition metal salt, resulting in an increase in treatment cost.

In the case the method for treating used absorbent articles of the present invention does not include the alkaline electrolyzed water treatment step (b) or the alkaline electrolyzed water treatment step (b) is carried out after the acidic electrolyzed water treatment step (a), metal ions are preferably introduced into the treatment tank that uses acidic electrolyzed water for the treatment liquid prior to introduction of the acidic electrolyzed water therein.

The method for treating used absorbent articles of the present invention preferably comprises a step (c2) for introducing metal ions into a treatment tank that uses alkaline electrolyzed water for the treatment liquid (Aspect 5). According to Aspect 5, in addition to the aforementioned effects, moisture contained in the superabsorbent polymer that composes the used absorbent article can be further dehydrated and removed. Since dehydration and removal of moisture in the superabsorbent polymer facilitates sedimentation of the superabsorbent polymer, the treatment efficiency (such as washing efficiency, disinfecting efficiency or rinsing efficiency) of the acidic electrolyzed water treatment step, alkaline electrolyzed water treatment step and rinsing step and the like can be further enhanced.

Specific examples of metal ions used in Aspect 5 are as previously described.

In the method for treating used absorbent articles of the present invention, in the case the alkaline electrolyzed water treatment step (b) is carried out prior to the acidic electrolyzed water treatment step (a), metal ions are preferably introduced into the treatment tank that uses alkaline electrolyzed water for the treatment liquid prior to introducing alkaline electrolyzed water therein.

The method for treating used absorbent articles of the present invention preferably further comprises a rinsing step (d) for rinsing the used absorbent article with water (Aspect 6). According to Aspect 6, in addition to the aforementioned effects, in the case of comprising a final rinsing step, soiling and bacteria can be rinsed off, making it possible to allow the recycled material such as recycled pulp following the acidic electrolyzed water treatment step (a) or the alkaline electrolyzed water treatment step (b) to more closely approach neutrality, while in the case of intermediate rinsing carried out after the alkaline electrolyzed water treatment step (b), residual organic matter can be rinsed off, thereby making it possible to enhance the bactericidal action in the subsequent acidic electrolyzed water treatment step. Hypochlorous acid demonstrates greater bactericidal action since it acts in the acidic range. In the case of intermediate rinsing after the acidic electrolyzed water treatment step (a), the effect is demonstrated of being able to rinse off eradicated organisms, water-soluble soiling and metal ion residue, the recycled material is in a state that more closely approaches neutrality, and subsequent alkaline washing effects are enhanced.

The method for treating used absorbent articles of the present invention preferably further comprises a dehydration step (e) for dehydrating used absorbent articles (Aspect 7). According to Aspect 7, since soiling and excess components can be effectively removed and excess moisture can be removed by dehydration, the effect can be demonstrated of being able to reduce the amount of energy required for subsequent drying.

Two or more of Aspects 1 to 7 can be combined in the method for treating used absorbent articles of the present invention.

Figure 1:
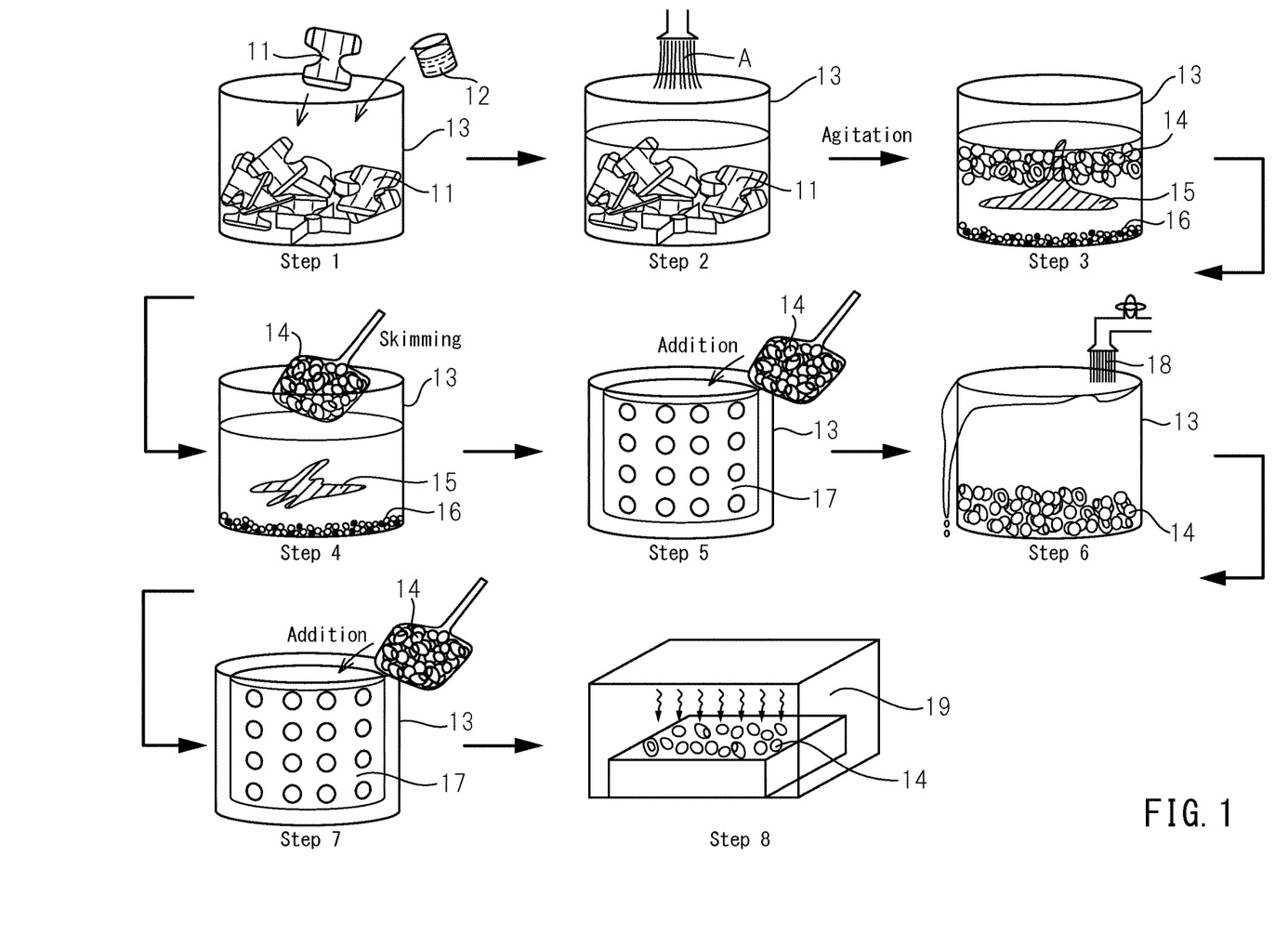
FIG. 1 is a drawing showing one embodiment of the method for treating used absorbent articles of the present invention.
Figure 2:
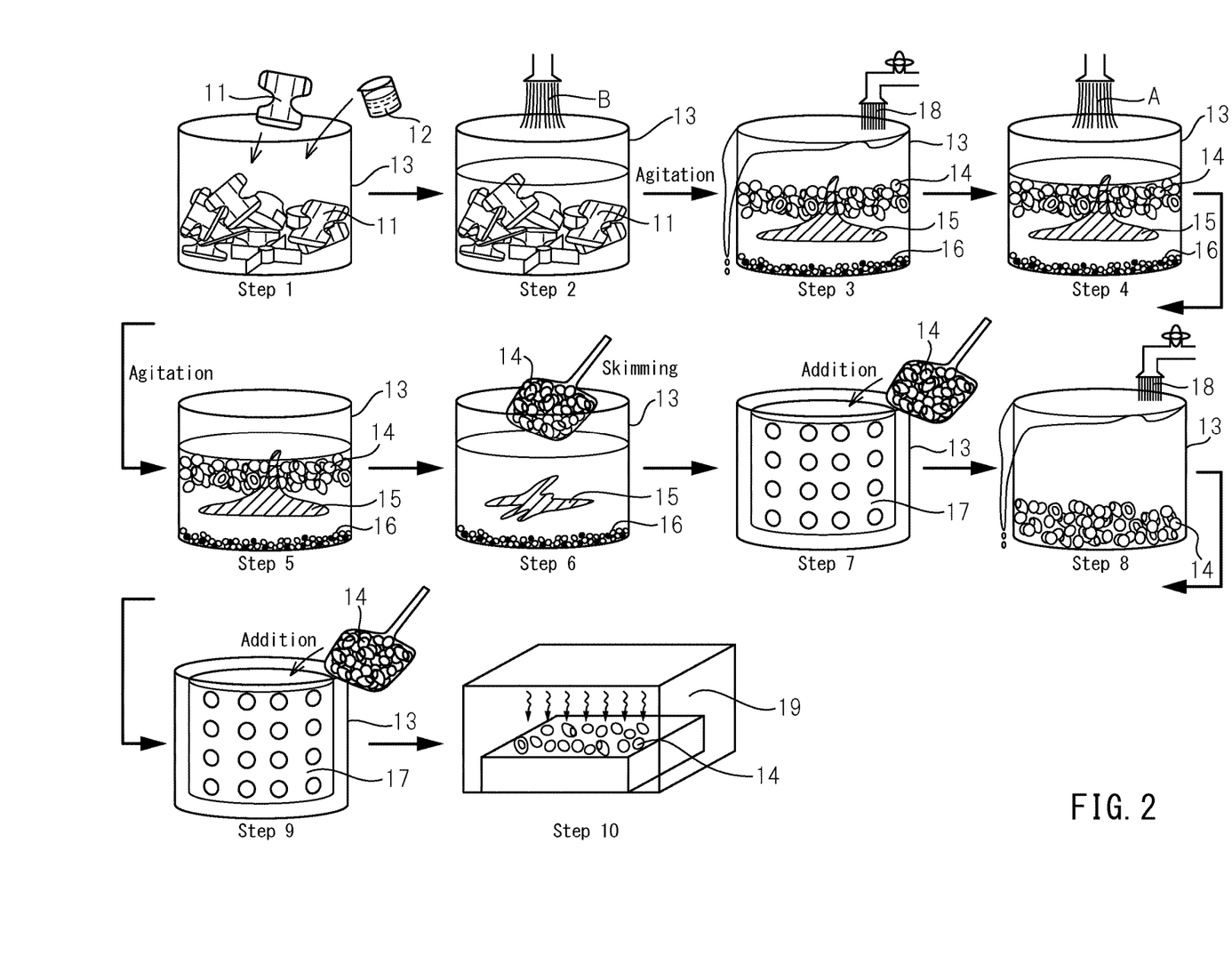
FIG. 2 is a drawing showing another embodiment of the method for treating used absorbent articles of the present invention.

The following provides a more detailed explanation of embodiments of the method for treating used absorbent articles according to the present invention based on FIGS. 1 and 2. Furthermore, the method for treating used absorbent articles according to the present invention is not limited to the embodiments of the present invention indicated in FIGS. 1 and 2 within a range that does not deviate from the object and gist of the present invention.

FIG. 1 is a drawing showing one embodiment of the method for treating used absorbent articles of the present invention. An explanation is first provided of acidic electrolyzed water treatment steps (step 1 and step 2). In step 1, a used disposable diaper (11) and calcium oxide (12) are placed in a treatment tank (13). Continuing, in step 2, acidic electrolyzed water (A) is added followed by agitation. After a prescribed amount of time has elapsed, pulp (14) floats near the upper portion of the treatment tank (13), nonwoven fabric, plastic and the like (15) float near the middle portion of the treatment tank (13), and superabsorbent polymer (16) settles in the lower portion of the treatment tank (13) in step 3. In step 4, the pulp (14) floating near the upper portion of the treatment tank (13) is skimmed off. In step 5, the pulp (14) that has been skimmed off is placed in a dehydrator (17) and dehydrated. In step 6, the dehydrated pulp (14) is rinsed with running water (18). Moreover, in step 7, the rinsed pulp (14) is again dehydrated by placing in the dehydrator (17). Finally, in step 8, the dehydrated pulp (14) is dried in a hot air dryer to obtain recycled pulp.

FIG. 2 is a drawing showing another embodiment of the method for treating used absorbent articles of the present invention. An explanation is first provided of the alkaline electrolyzed water treatment steps (steps 1 and 2). In step 1, the used disposable diaper (11) and the calcium oxide (12)

are placed in the treatment tank (13). Continuing, in step 2, alkaline electrolyzed water (B) is added followed by agitation. After a prescribed amount of time has elapsed, treatment water containing alkaline electrolyzed water is discharged, and the pulp (14) floating near the upper portion of the treatment tank (13), nonwoven fabric, plastic and the like (15) floating near the middle portion of the treatment tank (13), and the superabsorbent polymer (16) that settles in the lower portion of the treatment tank (13) are rinsed with the running water (18) in step 3. In step 4, the acidic electrolyzed water (A) is added followed by agitation. After a prescribed amount of time has elapsed, the pulp (14) again floats near the upper portion of the treatment tank (13), the nonwoven fabric, plastic and the like (15) float near the middle portion of the treatment tank (13), and the superabsorbent polymer (16) settles in the lower portion of the treatment tank (13) in step 5. In step 6, the pulp (14) floating near the upper portion of the treatment tank (13) is skimmed off. In step 7, the pulp (14) that has been skimmed off is placed in the dehydrator (17) and dehydrated. In step 8, the dehydrated pulp (14) is rinsed with the running water (18). Moreover, in step 9, the rinsed pulp (14) is again dehydrated by placing in the dehydrator (17). Finally, in step 10, the dehydrated pulp (14) is dried in a hot air dryer (19) to obtain recycled pulp.

EXAMPLES

Although the following provides an explanation of the present invention by indicating examples thereof, the present invention is not limited to these examples.

Example 1

Example 1-1

Evaluation of Washing Function 50 ml of acidic electrolyzed water (pH 3, generated with the ESS-ZERO Electrolyzed Water Sanitation System manufactured by Tech Corp.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of newly added acidic electrolyzed water. After allowing water to drain from the washed soiled cloth by placing in between two pieces of filter paper, the cloth was dried for 30 minutes with a hot air dryer at 105° C. The whiteness ($\Delta E$ value) of the dried soiled cloth was measured using a colorimeter (CR-300, Konica Minolta, Inc.) and used to quantify washing effect.

Example 1-2

Evaluation of Bactericidal Function

Minimum inhibitory concentration (MIC) of the acidic electrolyzed water was measured based on the standard test method of the Japanese Society of Chemotherapy followed by confirming the absence of growth 24 hours later to evaluate the minimum bactericidal concentration and determine if bactericidal effects are present at the concentration used in the example.

Example 1-3

Sample Preparation for Evaluating pH of Recycled Pulp

Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of acidic electrolyzed water (pH 3, generated with the ESS-ZERO Electrolyzed Water Sanitation System manufactured by Tech Corp.). After washing for 15 minutes, the liquid inside the washing tub was discharged followed by newly adding 6.5 L of acidic electrolyzed water (pH 3, formed with the ESS-ZERO Electrolyzed Water Sanitation System manufactured by Tech Corp.). After washing for 15 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub (dehydrator). The recycled pulp was rinsed for 15 minutes with running water (tap water) while still in the mesh pouch followed by again dehydrating for 5 minutes in the spin tub (dehydrator). The pulp was then dried for 24 hours with a hot air dryer at 105° C. Recycled pulp was obtained according to the aforementioned method.

(Evaluation of pH of Recycled Pulp)

1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).

(Residual Chlorine Concentration of Recycled Pulp)

5.00 g of pulp dried in the same manner as described above were eluted into 100 ml of physiological saline followed by measurement of the chlorine concentration thereof (JIS K 0102 33.2).

Example 2

Example 2-1

Evaluation of Washing Function 50 ml of alkaline electrolyzed water (pH 12, generated with the ESS-ZERO Electrolyzed Water Sanitation System manufactured by Tech Corp.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of acidic electrolyzed water (pH 3, generated with the ESS-ZERO Electrolyzed Water Sanitation System manufactured by Tech Corp.). After allowing water to drain from the washed soiled cloth by placing in between two pieces of filter paper, the cloth was dried for 30 minutes with a hot air dryer at 105° C. The whiteness ($\Delta E$ value) of the dried soiled cloth was measured using a colorimeter (CR-300, Konica Minolta, Inc.) and used to quantify washing effect.

Example 2-2

Evaluation of Bactericidal Function

Minimum inhibitory concentrations (MIC) of the alkaline electrolyzed water and acidic electrolyzed water were respectively measured based on the standard test method of the Japanese Society of Chemotherapy followed by confirming the absence of growth 24 hours later to evaluate the minimum bactericidal concentration and determine if bactericidal effects are present at the concentration used in Example 2-2.

Example 2-3

Sample Preparation for Evaluating pH of Recycled Pulp

Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of alkaline electrolyzed water (pH 12, generated with the ESS-ZERO Electrolyzed Water Sanitation System manufactured by Tech Corp.). After washing for 15 minutes, the liquid inside the washing tub was discharged followed by the addition of 6.5 L of acidic electrolyzed water (pH 3, formed with the ESS-ZERO Electrolyzed Water Sanitation System manufactured by Tech Corp.). After washing for 15 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub (dehydrator). The recycled pulp was rinsed for 15 minutes with running water (tap water) while still in the mesh pouch followed by again dehydrating for 5 minutes in the spin tub (dehydrator). The pulp was then dried for 24 hours with a hot air dryer at 105° C. Recycled pulp was obtained according to the aforementioned method.

(Evaluation of pH of Recycled Pulp)

1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).

(Residual Chlorine Concentration of Recycled Pulp)

5.00 g of pulp dried in the same manner as described above were eluted into 100 ml of physiological saline followed by measurement of the chlorine concentration thereof (JIS K 0102 33.2).

Example 3

Example 3-1

Evaluation of Washing Function 50 ml of acidic electrolyzed water (pH 3, generated with the ESS-ZERO Electrolyzed Water Sanitation System manufactured by Tech Corp.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of alkaline electrolyzed water (pH 12, generated with the ESS-ZERO Electrolyzed Water Sanitation System manufactured by Tech Corp.). After allowing water to drain from the washed soiled cloth by placing in between two pieces of filter paper, the cloth was dried for 30 minutes with a hot air dryer at 105° C. The whiteness (ΔE value) of the dried soiled cloth was measured using a colorimeter (CR-300, Konica Minolta, Inc.) and used to quantify washing effect.

Example 3-2

Evaluation of Bactericidal Function

Minimum inhibitory concentrations (MIC) of the acidic electrolyzed water and alkaline electrolyzed water were respectively measured based on the standard test method of the Japanese Society of Chemotherapy followed by confirming the absence of growth 24 hours later to evaluate the minimum bactericidal concentration and determine if bactericidal effects are present at the concentration used in Example 3-2.

Example 3-3

Sample Preparation for Evaluating pH of Recycled Pulp

Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of acidic electrolyzed water (pH 3, generated with the ESS-ZERO Electrolyzed Water Sanitation System manufactured by Tech Corp.). After washing for 15 minutes, the liquid inside the washing tub was discharged followed by the addition of 6.5 L of alkaline electrolyzed water (pH 12, formed with the ESS-ZERO Electrolyzed Water Sanitation System manufactured by Tech Corp.). After washing for 15 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub (dehydrator). The recycled pulp was rinsed for 15 minutes with running water (tap water) while still in the mesh pouch followed by again dehydrating for 5 minutes in the spin tub (dehydrator). The pulp was then dried for 24 hours with a hot air dryer at 105° C. Recycled pulp was obtained according to the aforementioned method.

(Evaluation of pH of Recycled Pulp)

1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).

(Residual Chlorine Concentration of Recycled Pulp)

5.00 g of pulp dried in the same manner as described above were eluted into 100 ml of physiological saline followed by measurement of the chlorine concentration thereof (JIS K 0102 33.2).

Comparative Example 1

Comparative Example 1-1

Evaluation of Washing Function 50 ml of tap water were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of newly added tap water. After allowing water to drain from the washed soiled cloth by placing in between two pieces of filter paper, the cloth was dried for 30 minutes with a hot air dryer at 105° C. The whiteness (ΔE value) of the dried soiled cloth was measured using a colorimeter (CR-300, Konica Minolta, Inc.) and used to quantify washing effect.

Comparative Example 1-2

Evaluation of Bactericidal Function
Minimum inhibitory concentration (MIC) of the tap water was measured based on the standard test method of the Japanese Society of Chemotherapy followed by confirming the absence of growth 24 hours later to evaluate the minimum bactericidal concentration and determine if bactericidal effects are present at the concentration used in the example.

Comparative Example 1-3

Sample Preparation for Evaluating pH of Recycled Pulp
Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of tap water. After washing for 30 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub. The recycled pulp was rinsed for 15 minutes with tap water while still in the mesh pouch followed by again dehydrating for 5 minutes in the spin tub. The recycled pulp was then dried for 24 hours with a hot air dryer at 105° C. Recycled pulp was obtained according to the aforementioned method.
(Evaluation of pH of Recycled Pulp)
1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).
(Residual Chlorine Concentration of Recycled Pulp)
5.00 g of pulp dried in the same manner as described above were eluted into 100 ml of distilled water followed by measurement of the chlorine concentration thereof (JIS K 0102 33.2).

Comparative Example 2

Comparative Example 2-1

Evaluation of Washing Function
50 ml of alkaline electrolyzed water (pH 12, generated with the ESS-ZERO Electrolyzed Water Sanitation System manufactured by Tech Corp.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of alkaline electrolyzed water. After allowing water to drain from the washed soiled cloth by placing in between two pieces of filter paper, the cloth was dried for 30 minutes with a hot air dryer at 105° C. The whiteness (ΔE value) of the dried soiled cloth was measured using a colorimeter (CR-300, Konica Minolta, Inc.) and used to quantify washing effect.

Comparative Example 2-2

Evaluation of Bactericidal Function
Minimum inhibitory concentrations (MIC) of the alkaline electrolyzed water was measured based on the standard test method of the Japanese Society of Chemotherapy followed by confirming the absence of growth 24 hours later to evaluate the minimum bactericidal concentration and determine if bactericidal effects are present at the concentration used in Comparative Example 2-2.

Comparative Example 3

Comparative Example 3-1

Evaluation of Washing Function
50 ml of 250 ppm sodium hypochlorite (prepared by diluting that purchased from Wako Pure Chemical Industries, Ltd.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of newly added sodium hypochlorite. After allowing water to drain from the washed soiled cloth by placing in between two pieces of filter paper, the cloth was dried for 30 minutes with a hot air dryer at 105° C. The whiteness (ΔE value) of the dried soiled cloth was measured using a colorimeter (CR-300, Konica Minolta, Inc.) and used to quantify washing effect.

Comparative Example 3-2

Evaluation of Bactericidal Function
Minimum inhibitory concentration (MIC) of the 250 ppm sodium hypochlorite was measured based on the standard test method of the Japanese Society of Chemotherapy followed by confirming the absence of growth 24 hours later to evaluate the minimum bactericidal concentration and determine if bactericidal effects are present at the concentration used in Comparative Example 3-2.

Comparative Example 3-3

Sample Preparation for Evaluating pH of Recycled Pulp
Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of 250 ppm sodium hypochlorite (prepared by diluting that purchased from Wako Pure Chemical Industries, Ltd.). After washing for 30 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub. The recycled pulp was rinsed for 15 minutes with tap water while still in the mesh pouch followed by again dehydrating for 5 minutes in the spin tub. The recycled pulp was then dried for 24 hours with a hot air dryer at 105° C. Recycled pulp was obtained according to the aforementioned method.
(Evaluation of pH of Recycled Pulp)
1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).

(Residual Chlorine Concentration of Recycled Pulp)

5.00 g of pulp dried in the same manner as described above were eluted into 100 ml of distilled water followed by measurement of the chlorine concentration thereof (JIS K 0102 33.2).

Comparative Example 4

Comparative Example 4-1

Evaluation of Washing Function 50 ml of 500 ppm sodium hypochlorite (prepared by diluting that purchased from Wako Pure Chemical Industries, Ltd.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of newly added 500 ppm sodium hypochlorite (prepared by diluting that purchased from Wako Pure Chemical Industries, Ltd.). After allowing water to drain from the washed soiled cloth by placing in between two pieces of filter paper, the cloth was dried for 30 minutes with a hot air dryer at 105° C. The whiteness ($\Delta E$ value) of the dried soiled cloth was measured using a colorimeter (CR-300, Konica Minolta, Inc.) and used to quantify washing effect.

Comparative Example 4-2

Evaluation of Bactericidal Function

Minimum inhibitory concentration (MIC) of the 500 ppm sodium hypochlorite was measured based on the standard test method of the Japanese Society of Chemotherapy followed by confirming the absence of growth 24 hours later to evaluate the minimum bactericidal concentration and determine if bactericidal effects are present at the concentration used in Comparative Example 4-2.

Comparative Example 4-3

Sample Preparation for Evaluating pH of Recycled Pulp

Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of 500 ppm sodium hypochlorite (prepared by diluting that purchased from Wako Pure Chemical Industries, Ltd.). After washing for 30 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub. The recycled pulp was rinsed for 15 minutes with tap water while still in the mesh pouch followed by again dehydrating for 5 minutes in the spin tub. The recycled pulp was then dried for 24 hours with a hot air dryer at 105° C. Recycled pulp was obtained according to the aforementioned method.

(Evaluation of pH of Recycled Pulp)

1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).

(Residual Chlorine Concentration of Recycled Pulp)

5.00 g of pulp dried in the same manner as described above were eluted into 100 ml of distilled water followed by measurement of the chlorine concentration thereof (JIS K 0102 33.2).

Comparative Example 5

Comparative Example 5-1

Evaluation of Washing Function 50 ml of 1000 ppm sodium hypochlorite (prepared by diluting that purchased from Wako Pure Chemical Industries, Ltd.) were placed in a 100 ml beaker. An artificially soiled cloth (EMPA111 manufactured by EMPA) cut into the shape of a square measuring 4 cm on a side was washed for 10 minutes while agitating at 500 rpm using a magnetic stirrer (RS-4DR, As One Corp.). After rinsing the washed soiled cloth with water, the cloth was continued to be washed for 10 minutes in 50 ml of newly added 1000 ppm sodium hypochlorite (prepared by diluting that purchased from Wako Pure Chemical Industries, Ltd.). After allowing water to drain from the washed soiled cloth by placing in between two pieces of filter paper, the cloth was dried for 30 minutes with a hot air dryer at 105° C. The whiteness ($\Delta E$ value) of the dried soiled cloth was measured using a colorimeter (CR-300, Konica Minolta, Inc.) and used to quantify washing effect.

Comparative Example 5-2

Evaluation of Bactericidal Function

Minimum inhibitory concentration (MIC) of the 1000 ppm sodium hypochlorite was measured based on the standard test method of the Japanese Society of Chemotherapy followed by confirming the absence of growth 24 hours later to evaluate the minimum bactericidal concentration and determine if bactericidal effects are present at the concentration used in Comparative Example 4-2.

Comparative Example 5-3

Sample Preparation for Evaluating pH of Recycled Pulp

Eight commercially available disposable diapers (Moony M Size, Unicharm Corp.) that had adsorbed 200 ml of physiological saline were placed in a twin tub compact washing machine (Harebare AST-01, Alumis Co., Ltd.). 80 g of CaO (Wako Pure Chemical Industries, Ltd.) were placed in the washing tub followed by the addition of 6.5 L of 1000 ppm sodium hypochlorite (prepared by diluting that purchased from Wako Pure Chemical Industries, Ltd.). After washing for 30 minutes, only the pulp that floated in the liquid in the washing tub was skimmed off followed by placing in a mesh pouch (measuring 25 cm on a side, N-No. 250HD, NBC Meshtec Inc.) and dehydrating for 5 minutes in the spin tub. The recycled pulp was rinsed for 15 minutes with tap water while still in the mesh pouch followed by again dehydrating for 5 minutes in the spin tub. The recycled pulp was then dried for 24 hours with a hot air dryer at 105° C. Recycled pulp was obtained according to the aforementioned method.

(Evaluation of pH of Recycled Pulp)

1.00 g of the dried pulp was weighed out into a beaker followed by the addition of 10 ml of physiological saline. After gently stirring with a glass rod, the pulp was allowed to stand undisturbed for 10 minutes followed by measurement of the liquid inside the beaker with a pH meter (AS-212, As One Corp.).

(Residual Chlorine Concentration of Recycled Pulp)

5.00 g of pulp dried in the same manner as described above were eluted into 100 ml of distilled water followed by measurement of the chlorine concentration thereof (JIS K 0102 33.2).

The results of Examples 1 to 3 and Comparative Examples 1 to 5 are shown in the following Table 1. As shown in Table 1, the results of Example 2 for washing function were such that the level of whiteness returned to nearly the original level of whiteness, while the results of Examples 1 and 3 were such that whiteness (coloring) was of a level that does not present a problem in terms of practical use. Furthermore, a difference in ΔE value of 1.00 is generally considered to be indistinguishable.

Bactericidal effect was evaluated by measuring minimum bactericidal concentration for each microorganism (*Escherichia coli* or *Staphylococcus aureus*), and all of the results exhibited effects of bactericidal action with the exception of the results of Comparative Examples 1 and 2.

The results for residual chlorine concentration were such that chlorine was not detected (less than 1 ppm) according to the results of Examples 1 and 2. Although the results of Comparative Example 1 were such that residual chlorine was not detected, this is because tap water was used for washing.

The pH of the recycled pulp was such that the results of Examples 1 and 2 indicated pH values within a pH range that does not present problems in terms of practical use (pH 3.1 to 9.8). The pH values of Comparative Examples 3 to 5, in which sodium hypochlorite was used, were outside the pH range that does not present problems in terms of practical use (pH 3.1 to 9.8).

TABLE 1

|  | Washing Function ΔE Soiled cloth: ΔE = 50.0 Original cloth: 9.4 | Bactericidal Effect | | Residual Chlorine ppm Less than 1 ppm | pH of Recycled Pulp pH 3.1-9.8 |
| --- | --- | --- | --- | --- | --- |
|  |  | *E. coli* | *S. aureus* |  |  |
| Example 1 | 19.5 | − | − | <1 ppm (not detected) | 8.3 |
| Example 2 | 9.3 | − | − | <1 ppm (not detected) | 9.5 |
| Example 3 | 20.2 | − | − | — | — |
| Comp. Ex. 1 | 41.3 | + | + | <1 ppm (not detected) | 12.2 |
| Comp. Ex. 2 | 11.6 | + | + | — | — |
| Comp. Ex. 3 | 24.9 | − | − | 1 | 12.3 |
| Comp. Ex. 4 | 24.6 | − | − | 1 | 12.2 |
| Comp. Ex. 5 | 19.7 | − | − | 1 | 12.0 |

BRIEF DESCRIPTION OF THE REFERENCE SYMBOLS

11 Disposable diaper (absorbent article)
12 Calcium oxide
13 Treatment tank
14 Pulp
15 Nonwoven fabric, plastic and the like
16 Superabsorbent polymer
17 Dehydrator
18 Running water
19 Hot air dryer
A Acidic electrolyzed water
B Alkaline electrolyzed water

The invention claimed is:

1. A method for recovering pulp from used absorbent articles comprising:
    (a) obtaining used absorbent articles having absorbent bodies that comprise pulp and a superabsorbent polymer;
    (b) subjecting the used absorbent articles to an acidic electrolyzed water treatment step for treating the used absorbent articles in a treatment tank that uses acidic electrolyzed water containing calcium oxide for the treatment liquid thereof;
    (c) an alkaline electrolyzed water treatment step for treating the used absorbent articles in a treatment tank that uses alkaline electrolyzed water for the treatment liquid thereof; and
    (d) recovering pulp from the absorbent articles after step (c),
    wherein the alkaline electrolyzed water treatment step (c) is carried out after the acidic electrolyzed water treatment step (b).
2. The method according to claim 1, further comprising:
    (f) a rinsing step for rinsing the used absorbent articles with water.
3. The method according to claim 1, further comprising:
    (g) a dehydration step for dehydrating the used absorbent articles.
4. The method according to claim 1, further comprising:
    (e2) a step for introducing metal ions into the treatment tank that uses alkaline electrolyzed water for the treatment liquid thereof.

* * * * *